United States Patent
Pagan

[11] Patent Number: 6,116,243
[45] Date of Patent: *Sep. 12, 2000

[54] LARYNGEAL MASK ASSEMBLIES

[75] Inventor: Eric Pagan, Hythe, United Kingdom

[73] Assignee: Smiths Industries Public Limited Company, London, United Kingdom

[*] Notice: This patent is subject to a terminal disclaimer.

[21] Appl. No.: 09/037,994

[22] Filed: Mar. 11, 1998

[30] Foreign Application Priority Data

Mar. 18, 1997 [GB] United Kingdom ............... 9705586

[51] Int. Cl.$^7$ .................................................. A61M 16/00
[52] U.S. Cl. ............................... 128/207.15; 128/207.14
[58] Field of Search ................. 128/200.26, 207.14, 128/207.15; 604/96–103

[56] References Cited

U.S. PATENT DOCUMENTS

| | | | |
|---|---|---|---|
| 4,509,514 | 4/1985 | Brain | 128/207.15 |
| 5,297,547 | 3/1994 | Brain | 128/207.15 |
| 5,584,290 | 12/1996 | Brain | 128/207.15 |
| 5,720,275 | 2/1998 | Patil et al. | 128/200.26 |
| 5,743,254 | 4/1998 | Parker | 128/200.26 |
| 5,771,889 | 6/1998 | Pagan | 128/207.15 |
| 5,878,745 | 3/1999 | Brain | 128/207.15 |
| 5,896,858 | 4/1999 | Brain | 128/207.15 |
| 5,983,897 | 11/1999 | Pagan | 128/207.15 |
| 6,012,452 | 1/2000 | Pagan | 128/200.26 |

*Primary Examiner*—John G. Weiss
*Assistant Examiner*—Joseph F. Weiss
*Attorney, Agent, or Firm*—Pollock, Vande Sande & Amernick, R.L.L.P.

[57] ABSTRACT

The mask portion at the patient end of a laryngeal mask assembly is formed by a mount member having an outwardly projecting, oval plate and by two separate semi-annular cuffs bonded to opposite sides of the plate. An inflation lumen opens into one cuff, the plate having several holes through it so that the inflation fluid flows also to the other cuff.

6 Claims, 1 Drawing Sheet

LARYNGEAL MASK ASSEMBLIES

BACKGROUND OF THE INVENTION

This invention relates to laryngeal mask assemblies.

It is common practice to use an airway known as a laryngeal mask for the administration of anaesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are described in, for example, U.S. Pat. No. 5,355,879, U.S. Pat. No. 5,305,743, U.S. Pat. No. 5,297,547, U.S. Pat. No. 5,282,464, GB 2267034, U.S. Pat. No. 5,249,571, U.S. Pat. No. 5,241,956, U.S. Pat. No. 5,303,697, GB 2249959, GB 2111394, EP 448878, U.S. Pat. No. 4,995,388, GB 2205499, GB 2128561 and GB22988797.

Laryngeal masks have several advantages over endotracheal tubes, which are longer and seal with the trachea below the vocal folds. One problem with laryngeal mask airways, however, is that it is difficult to provide the cuff, which is of relatively complex shape, at low cost.

SUMMARY OF THE INVENTION

It is an object of the present invention to provide an improved laryngeal mask assembly.

According to the present invention there is provided a laryngeal mask assembly comprising a tube with a mask portion at its patient end, the tube having an opening into the center of the mask portion, the mask portion including a mount member joined with the patient end of the tube, the mount member having an outwardly-projecting plate member, the mask portion including a first cuff member attached to one side of the plate member, a second cuff member attached to the opposite side of the plate member, and at least one fluid passage extending between the two cuff members, and the assembly including an inflation passage opening into one of the cuff members so that fluid supplied to the one cuff member is communicated to both cuff members via the fluid passage between the cuffs The fluid passage may extend through the plate member and is preferably provided by a plurality of holes through the plate member. One of the cuff members may have inner and outer rims, the inner and outer rims being bonded to one side of the plate member to define an annular space between the cuff member and the plate member. Preferably, both cuff members have inner and outer rims bonded to respective opposite sides of the plate member. The first and second cuffs may have different properties from one another.

A laryngeal mask airway assembly according to the present invention, will now be described, by way of example, with reference to the accompanying drawing.

DETAILED DESCRIPTION OF THE PREFERRED EMBODIMENT

Figure 1:
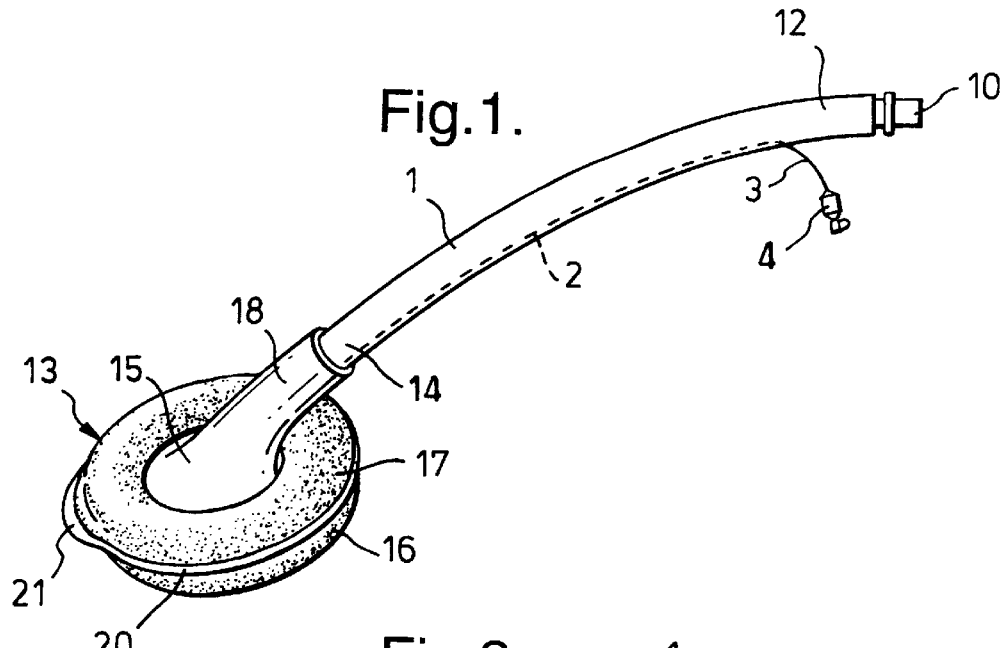
FIG. 1. is a side elevation view of the assembly.
Figure 2:
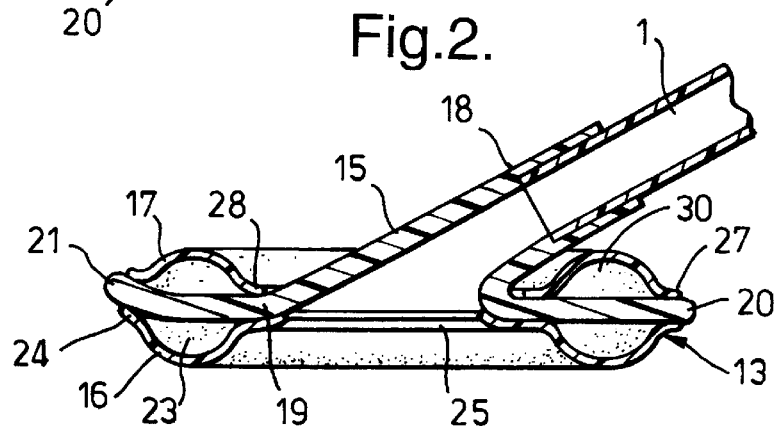
FIG. 2. is a sectional side elevation view of the patient end of the assembly to an enlarged scale.
Figure 3:
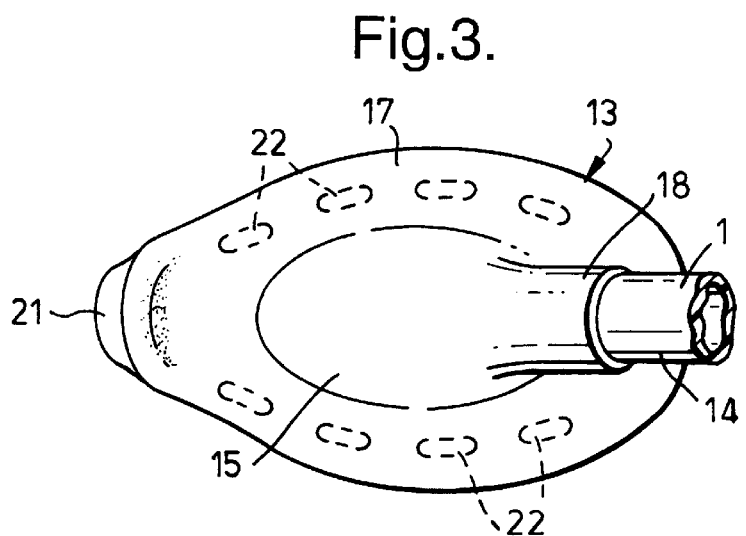
FIG. 3. is a view from above of the patient end of the assembly.

The assembly comprises a bendable tube 1 of a plastic material, such as PVC, with a coupling 10 at its machine end 12. The tube 1 is curved along its length and has a mask portion 13 at its patient end 14.

The tube 1 is extruded with an inflation lumen 2 within its wall. The lumen 2 is connected towards the machine end of the assembly to an inflation line 3 with an inflation indicator and connector 4. The opposite, patient end of the inflation lumen 2 opens into the mask portion 13.

The mask portion 13 comprises a mount member 15 and two cuff members 16 and 17. The mount member 15 is molded from a bendable plastics material, such as PVC. The mount member 15 has a hollow cylindrical sleeve 18 at its rear end, in which the forward, patient end 14 of the tube 1 is inserted and joined. The forward, patient end 19 of the mount member 15 has a substantially flat plate 20 with a generally elliptical or egg-shaped outline, which projects outwardly of the sleeve 18 at an angle of about 30°. The forward edge of the plate 20 is curved upwardly to form a leading tip 21. Several air vent holes 22 are spaced around the plate 20 and allow air to flow through the thickness of the plate.

The cuff members 16 and 17 are both blow molded from a flexible, resilient plastic material, such as PVC, polyurethane, silicone, EVA, TPE, polyether block amide or the like. The cuff members could be formed in other ways, such as by vacuum forming, pressure vacuum forming or injection molding. Alternatively, the cuff members could be flat sheets, which might have elastomeric properties or be laminates with reinforcing. The lower, patientend cuff member 16 has a semi-annular shape with a periphery conforming to the outline of the plate 20. An annular recess or channel 23 extends around the upper surface of the cuff, within a peripheral rim 24. In the center of the cuff member 16 there is an aperture 25 of oval shape, which conforms to the shape of the opening of the patient end of sleeve 18. The cuff member 16 is bonded to the lower, patient side of the plate 20 both around the rim 24 and around the edge of the aperture 25 to enclose an annular space between the lower surface of the plate and the channel 23. The upper cuff member 17 is similar in shape to the lower cuff member 16 but is arranged upside down. The upper cuff member 17 has a peripheral rim 27 and an inner rim 28 bonded to the upper surface of the plate 20, on either side of an annular channel 30. The upper channel 30 communicates with the inflation lumen 2 by means of a channel in the mount member 15, or an interconnecting tube, so that gas supplied to the inflation lumen inflates the upper cuff member 17 and, because the gas flows through the air vents 22, it also inflates the lower cuff member 16.

The leading tip 21 projects forwardly slightly beyond the upper and lower cuff members 16 and 17 so as to provide a stiffer leading edge to help guide the mask portion 13 into the correct location.

By forming the cuff in two parts 16 and 17, it facilitates manufacture and assembly, enabling a wide range of different shapes and sizes to be produced. It also enables the cuff to have different properties on its upper and lower sides.

What I claim is:

1. A laryngeal mask assembly comprising: a tube having a machine end and a patient end; and a mask portion at said patient end of said tube, wherein said tube has an opening into a center of said mask portion, wherein said mask portion includes a mount member joined with said patient end of said tube, wherein said mount member has an outwardly-projecting plate member, wherein said mask portion includes a first cuff member attached to one side of said plate member, a second cuff member attached to the opposite side of the plate member, and at least one fluid passage extending between said two cuff members, and wherein said assembly includes an inflation passage opening into one of said cuff members so that fluid supplied to said one cuff member is communicated to both said cuff members via said fluid passage.

2. A laryngeal mask assembly according to claim 1, wherein said fluid passage extends through said plate member.

3. A laryngeal mask assembly according to claim 2, wherein said fluid passage is provided by a plurality of holes through said plate member.

4. A laryngeal mask assembly according to claim 1, wherein one of said cuff members has inner and outer rims, and wherein said inner and outer rims are bonded to one side of said plate member to define an annular space between said cuff member and said plate member.

5. A laryngeal mask assembly according to claim 4, wherein both said cuff members have inner and outer rims, and wherein said cuff members are bonded to respective opposite sides of said plate member.

6. A laryngeal mask assembly comprising: a tube having a machine end and a patient end; a mount member, said mount member having a sleeve joined to said patient end of said tube, and a plate member of oval shape projecting outwardly from said sleeve; a first cuff member bonded to a patient side of said plate member; and a second cuff member bonded to an opposite side of said plate member, wherein said assembly includes a cuff inflation passage extending along said tube and opening into one of said cuff members, and wherein said plate member has at least one hole therethrough so that fluid supplied to said one cuff member flows through said hole to said other cuff member.

* * * * *